US010703736B2

(12) United States Patent
Caruel et al.

(10) Patent No.: US 10,703,736 B2
(45) Date of Patent: Jul. 7, 2020

(54) CONFIGURATIONAL STEREOISOMER OF BROMADIOLONE, COMPOSITION AND RODENTICIDE BAIT COMPRISING SAME, AND METHOD FOR CONTROLLING TARGET RODENT PESTS

(71) Applicants: LIPHATECH, Pont-du-casse (FR); INSTITUT ENSEIGNEMENT SUPERIEUR ET RECHERCHE EN ALIMENTATION SANTE ANIMALE SCIENCES AGRONOMIQUES ET ENVIRONNEMENT (VET AGRO SUP), Marcy L'etoile (FR)

(72) Inventors: Hervé Caruel, Moncaut (FR); Etienne Benoit, Lyons (FR); Isabelle Fourel, Miribel (FR); Virginie Lattard, Lyons (FR)

(73) Assignees: LIPHATECH, Pont-du-casse (FR); INSTITUT ENSEIGNEMENT SUPERIEUR ET RECHERCHE EN ALIMENTATION SANTE ANIMALE SCIENCES AGRONOMIQUES ET ENVIRONNEMENT (VET AGRO SUP), Marcy L'etoile (FR)

( * ) Notice: Subject to any disclaimer, the term of this patent is extended or adjusted under 35 U.S.C. 154(b) by 16 days.

(21) Appl. No.: 16/061,203

(22) PCT Filed: Dec. 6, 2016

(86) PCT No.: PCT/EP2016/079867
§ 371 (c)(1),
(2) Date: Jun. 11, 2018

(87) PCT Pub. No.: WO2017/097754
PCT Pub. Date: Jun. 15, 2017

(65) Prior Publication Data
US 2018/0362490 A1    Dec. 20, 2018

(30) Foreign Application Priority Data
Dec. 11, 2015  (FR) ..................... 15 62170

(51) Int. Cl.
*A01N 25/00*  (2006.01)
*C07D 311/56*  (2006.01)
*A01N 43/16*  (2006.01)
*B01D 15/38*  (2006.01)
*C07B 57/00*  (2006.01)

(52) U.S. Cl.
CPC .......... *C07D 311/56* (2013.01); *A01N 25/004* (2013.01); *A01N 43/16* (2013.01); *B01D 15/3833* (2013.01); *C07B 57/00* (2013.01); *C07B 2200/07* (2013.01)

(58) Field of Classification Search
None
See application file for complete search history.

(56) References Cited

U.S. PATENT DOCUMENTS 4,783,481 A * 11/1988 Swaine .................. A01N 43/16
514/457

FOREIGN PATENT DOCUMENTS

EP        0 147 052 A2    7/1985
EP        2 090 164 B1    8/2009
WO    WO-2007066160 A1 *  6/2007    ............. C07B 57/00

OTHER PUBLICATIONS

Avdagic, Amir et al: "Long-distance control in stereoselective reduction of 3-[3-(4'-bromo[1,1'-biphenyl]-4-yl)-3-keto-1-phenylpropyl]-4-hydroxy-2H-1-benzopyran-2-one: relative configuration of prevailing diastereomer and absolute configuration of its enantiomers", Chirality, vol. 9, No. 5/6, 1997, pp. 512-522, XP002755641, DOI: 10.1002/(SICI)1520-636X(1997)9:5/6<512::AID-CHIR18>3.3.CO;2-5 *.
Hunter, K. et al: "Determination of diastereoisomers of bromadiolone, an anticoagulant rodenticide, in animal tissues by high-performance liquid chromatography", Journal of Chromatography, vol. 435, No. 1, 1988, pp. 83-95, XP002755642, DOI: 10.1016/S0021-9673(01)82165-8.
Koeppen et al: "Liquid chromatographic determination of bromadiolone in rodent baits", Journal of the Association of Official Analytical Chemists, the Association, Arlington, VA, US, vol. 73, No. 3, Jan. 1, 1990 (Jan. 1, 1990), pp. 429-430, XP009186066, ISSN: 0004-5756.
International Search Report, dated Feb. 9, 2017, from corresponding PCT/EP2016/079867 application.

* cited by examiner

*Primary Examiner* — Susan T Tran
(74) *Attorney, Agent, or Firm* — IPSILON USA, LLP (57) ABSTRACT

Disclosed is a configurational stereoisomer, named enantiomer $E_1$, of bromadiolone having, by chromatographic analysis of bromadiolone including four configurational stereoisomers of bromadiolone performed under the conditions described below, a retention time $t_1$ having a value such that $t_1 < t_2 < t_3 < t_4$; $t_2$, $t_3$ and $t_4$ being the retention times of the configurational stereoisomers of bromadiolone different from the enantiomer $E_1$, the analysis being performed at a temperature of 27.3° C.

20 Claims, 2 Drawing Sheets

CONFIGURATIONAL STEREOISOMER OF BROMADIOLONE, COMPOSITION AND RODENTICIDE BAIT COMPRISING SAME, AND METHOD FOR CONTROLLING TARGET RODENT PESTS

The invention relates to a configurational stereoisomer of bromadiolone, to a composition and a rodenticidal bait comprising such a configurational stereoisomer of bromadiolone and to a process for controlling target rodent pests. The invention thus relates to the technical field of controlling the development of populations of target rodent pests.

It is known practice to use poisons in the form of rodenticidal baits against target rodent pests. It is known from EP 2 090 164 that bromadiolone is a second-generation anticoagulant acting in a single dose. A bait comprising bromadiolone is also known, the proportion of bromadiolone in the bait being 50 ppm.

Such a bait is liable to be consumed by animals other than target rodent pests when it is made available to target rodent pests. It may be consumed directly (primary consumption) by domestic animals or pets. It may also be consumed accidentally by humans. Such consumption may result in poisoning, which may be lethal, of these domestic animals, pets or humans.

In addition, a fraction of the bromadiolone of these rodenticidal baits may be ingested (secondary consumption) by animals—especially by birds—which prey on weakened target rodent pests that have consumed such a rodenticidal bait, or by animals which carrion-feed on rodent pests that have died from having consumed such a rodenticidal bait. This secondary consumption is liable in the long term to result in the death of these predatory or carrion-feeding animals, which may be animals—especially birds—belonging to protected species.

The invention is thus directed towards overcoming these drawbacks by proposing a configurational stereoisomer of bromadiolone, a composition and a rodenticidal bait comprising such a configurational stereoisomer of bromadiolone and a process for controlling target rodent pests, which are effective for controlling populations of target rodent pests and can also limit the risks of poisoning of non-target animals—especially domestic animals, pets or humans—which accidentally consume such a rodenticidal bait.

The invention is also directed towards overcoming these drawbacks by proposing a configurational stereoisomer of bromadiolone, a composition and a rodenticidal bait comprising such a configurational stereoisomer of bromadiolone and a process for controlling target rodent pests, which are effective for controlling populations of target rodent pests and can also limit the risks of secondary poisoning of domestic animals (pets or reared animals) or wild animals—for example foxes or birds—which prey on weakened target rodent pests that have consumed the rodenticidal bait or which carrion-feed on target rodent pests that died from being poisoned.

The invention is also directed towards proposing a configurational stereoisomer of bromadiolone, a composition and a rodenticidal bait comprising such a configurational stereoisomer of bromadiolone and a process for controlling target rodent pests, the use of which is in accordance with the rules of good practice, especially with respect to the protection of birds, and in particular birds of prey.

The invention is also directed towards proposing a configurational stereoisomer of bromadiolone, a composition and a rodenticidal bait comprising such a configurational stereoisomer of bromadiolone and a process for controlling target rodent pests, which are environmentally friendly and friendly to human health and to the health of non-target animals, especially birds, and in particular birds of prey.

The invention is also directed towards proposing a configurational stereoisomer of bromadiolone, a composition and a rodenticidal bait comprising such a configurational stereoisomer of bromadiolone and a process for controlling target rodent pests, which make it possible to use only a small dose of bromadiolone to control a population of target rodent pests.

The invention is also directed towards proposing a configurational stereoisomer of bromadiolone, a composition and a rodenticidal bait comprising such a configurational stereoisomer of bromadiolone and a process for controlling target rodent pests, which are able to be used for controlling target rodent pests that are resistant to known baits for controlling target rodent pests.

The invention is thus directed towards proposing an alternative to known rodenticidal baits.

To do this, the invention relates to a configurational stereoisomer, named enantiomer $E_1$, of bromadiolone having, by chromatographic analysis of a bromadiolone composition comprising four configurational stereoisomers of bromadiolone performed under the conditions described hereinbelow, a retention time $t_1$ having a value such that $t_1 < t_2 < t_3 < t_4$; $t_2$, $t_3$ and $t_4$ being the retention times of the configurational stereoisomers of bromadiolone different from said enantiomer $E_1$, said analysis being performed at a temperature of 27.3° C. and under the following conditions:

on a high-pressure liquid chromatography column of dimensions 150×2 mm, and containing a chiral stationary phase constituted of particles of cellulose tris(3,5-dimethylphenyl carbamate), said particles having a mean size of 3 m and having a mean pore size of 1000 Å;

using, as liquid mobile phase, a mixture formed from acetonitrile (A) and water comprising 0.1% by volume of formic acid (B), with an A/B volume ratio of 80/20 and with a flow rate of the liquid mobile phase in the chromatography column of 0.25 mL/minute;

by injection into the chromatography column of a volume of 1 μL of bromadiolone composition at a concentration of 1 μg of bromadiolone per millilitre of acetonitrile.

Throughout the text:

the term "bromadiolone" denotes the compound 3-[3-(4'-bromo[1,1'-biphenyl]-4-yl)-3-hydroxy-1-phenylpropyl]-4-hydroxy-2H-1-benzopyran-2-one or 3-[3-[4-(4-bromophenyl)phenyl]-3-hydroxy-1-phenylpropyl]-2-hydroxychromen-4-one of formula (I) below:

in which are represented the numbers of carbons 1 and 3 of the 3-hydroxy-1-phenylpropyl group;

the term "stereoisomers" denotes isomers of the same semi-structural formula, but in which the relative position of the atoms differs in space. The term "configurational stereoisomers" denotes stereoisomers for which conversion from one to the other of these configurational stereoisomers requires the cleavage/reformation of an interatomic covalent bond. Thus, the term "configurational stereoisomers" denotes stereoisomers which are not conformational isomers (or "rotamers", for which conversion from one to the other of the conformational isomers is accompanied only by rotation of a part of the molecule about the axis of a σ (sigma) bond formed by axial orbital overlap);

the term "amount" means a molar amount, a mass amount or a volume amount. The proportions are thus proportions of a molar amount relative to a molar amount, of a mass amount relative to a mass amount, or of a volume amount relative to a volume amount;

the term "substantially" indicates, in the usual manner, that a structural or functional characteristic should not be taken as marking an abrupt discontinuity, which would have no physical meaning, but covers not only this structure or this function, but also slight variations of this structure or of this function which produce, in the technical context under consideration, an effect of the same nature, or else of the same degree;

the expressions "high-pressure liquid chromatography" or "high-performance liquid chromatography" (HPLC) denote "HPLC" chromatography or "High Performance Liquid Chromatography"; and the term "retention time" denotes the time, measured at the top of the peak in the chromatogram, for which a compound is retained on a chromatography column.

The invention thus relates to said enantiomer $E_1$ in isolated form, which has the property of being able to be eluted first, under the chromatography conditions described above, relative to the four configurational stereoisomers of bromadiolone.

The inventors have observed that analysis of bromadiolone by high-pressure liquid chromatography under the conditions described above reveals four signals or peaks corresponding to four compounds of the same chemical structural formula and corresponding to formula (I) of bromadiolone. Two of the signals detected correspond to one of the diastereoisomers of bromadiolone, the other two signals corresponding to the other bromadiolone diastereoisomer. One of the two diastereoisomers of bromadiolone is a configurational stereoisomer of bromadiolone in which carbons 1 and 3 of the 3-hydroxy-1-phenylpropyl group are of identical absolute configuration. The other of the two diastereoisomers of bromadiolone is a configurational stereoisomer of bromadiolone in which carbons 1 and 3 of the 3-hydroxy-1-phenylpropyl group have different absolute configurations, said absolute configurations being determined according to the Cahn-Ingold-Prelog (CIP) sequential priority and nomenclature rules.

They determined, by analysis of preparations of bromadiolone comprising variable proportions of the two diastereoisomers of bromadiolone, that the two compounds corresponding to the signal with a retention time ($t_1$) having a value of the order of 4.3 minutes and to the signal with a retention time ($t_2$) having a value of the order of 5.0 minutes correspond to the two enantiomers of one of the two diastereoisomers of bromadiolone and that the two compounds corresponding to the signal with a retention time ($t_3$) having a value of the order of 6.3 minutes and to the signal with a retention time ($t_4$) having a value of the order of 8.8 minutes correspond to the two enantiomers of the other of the two diastereoisomers of bromadiolone.

On account of slight variations in the chromatographic conditions—especially of the variations in temperature of the chromatography column—said enantiomer $E_1$ may have a retention time ($t_1$) with a value of between 4.1 minutes and 4.4 minutes, the retention time ($t_1$) of said enantiomer $E_1$ being less than the retention time ($t_2$) of another configurational stereoisomer, named enantiomer $E_2$, of a diastereoisomer, named diastereoisomer $D_{1,2}$, of bromadiolone, the retention time ($t_2$) possibly having a value of between 4.8 minutes and 5.2 minutes.

For the same reasons, said enantiomer $E_3$ may have a retention time ($t_3$) with a value of between 6.0 minutes and 6.6 minutes, the retention time ($t_3$) of said enantiomer $E_3$ being less than the retention time of another configurational stereoisomer, named enantiomer $E_4$, of a diastereoisomer, named diastereoisomer $D_{3,4}$, of bromadiolone, which is eluted fourth, under the chromatographic conditions described above, relative to the four configurational stereoisomers of bromadiolone and with a retention time $t_4$ having a value of between 8.3 minutes and 9.0 minutes.

The retention time values $t_1$, $t_2$, $t_3$ and $t_4$ are thus liable to vary, according to the chromatography conditions and especially with the temperature of the chromatography column. However, under these chromatographic conditions (choice of these mobile and stationary phases), the order of elution of the configurational stereoisomers of bromadiolone remains unchanged.

Said enantiomer $E_1$ according to the invention is thus obtained in a form separate from the enantiomers of said diastereoisomer $D_{3,4}$ and in a form separate from said enantiomer $E_2$ of said diastereoisomer $D_{1,2}$. It is possible to perform such a separation by high-pressure liquid chromatography on a LUX® Cellulose-1 chiral column (00F-4458-B0, Phenomenex®, Le Pecq, France). Where appropriate, it is possible successively to perform several high-pressure liquid chromatography steps on a chiral column for the purposes of obtaining the desired amount of said enantiomer $E_1$ in the desired purity. It is also possible to perform such a separation by high-pressure liquid chromatography on a preparative chiral column, i.e. on a chromatography column of larger dimensions—especially with an inside diameter of greater than 2 mm—and in which the stationary phase has a particle size of greater than 3 m. Said enantiomer $E_1$ purified and isolated from the other configurational stereoisomers of bromadiolone is obtained by removal of the mobile phase from the collected fraction containing said enantiomer $E_1$.

It was not previously known how to separate the configurational stereoisomers of bromadiolone and the enantiomers of said diastereoisomer $D_{1,2}$. Under these experimental conditions, the enantiomers ($E_1$ and $E_2$) of said diastereoisomer $D_{1,2}$ are separated and purified by high-pressure liquid chromatography.

Under these chromatographic conditions, the enantiomers of said diastereoisomer $D_{3,4}$ are also separated and purified. One of the enantiomers, named enantiomer $E_3$, of said diastereoisomer $D_{3,4}$ is eluted third, under the chromatography conditions described above, relative to the four configurational stereoisomers of bromadiolone. Under the conditions described above, said enantiomer $E_3$ has a retention time ($t_3$) with a value of between 6.0 minutes and 6.4 minutes. The other enantiomer, named enantiomer $E_4$, of said diastereoisomer $D_{3,4}$ is eluted fourth, under the chromatography conditions described above, relative to the four configurational stereoisomers of bromadiolone. Under the conditions described above, said enantiomer $E_4$ has a retention time ($t_4$) with a value of between 8.3 minutes and 9.0 minutes, such that the enantiomers $E_3$ and $E_4$ of said diastereoisomer $D_{3,4}$ are separated and purified by high-pressure liquid chromatography on a chiral column under these conditions.

The invention thus also relates to a chromatographic process for separating the configurational stereoisomers of bromadiolone—especially enantiomers $E_1$ and $E_2$ of said diastereoisomer $D_{1,2}$ and enantiomers $E_3$ and $E_4$ of said diastereoisomer $D_{3,4}$—of bromadiolone. The invention thus relates to such a chromatographic process for obtaining said enantiomer $E_1$ according to the invention, in which:

a high-pressure liquid chromatography column of dimensions 150×2 mm, and containing a chiral stationary phase constituted of cellulose tris(3,5-dimethylphenyl carbamate) particles, is chosen, said particles having a mean size of 3 µm and having a mean pore size of 1000 Å;

a mixture formed from acetonitrile (A) and water comprising 0.1% by volume of formic acid (B), with an A/B volume ratio of 80/20, is chosen as liquid mobile phase;

the separation is performed at room temperature;

a liquid composition containing said enantiomer $E_1$ dissolved in acetonitrile is introduced into the top of the chromatography column; and then the liquid mobile phase is passed at a flow rate of 0.25 mL/min through the chromatography column after the liquid composition, and a fraction of the mobile phase comprising said enantiomer $E_1$ is collected at the column outlet, separately from the configurational stereoisomers of bromadiolone different from said enantiomer $E_1$, and with a retention time $t_1$ having a value such that $t_1 < t_2 < t_3 < t_4$; $t_2$, $t_3$ and $t_4$ being the retention times of each of the configurational stereoisomers of bromadiolone different from said enantiomer $E_1$; and the liquid mobile phase of said fraction is removed so as to obtain said enantiomer $E_1$.

The invention also relates to a configurational stereoisomer—in particular said enantiomer $E_1$—of bromadiolone obtained via a process according to the invention.

The invention also relates to a composition comprising said enantiomer $E_1$, with the exclusion of a racemic mixture of said enantiomer $E_1$ and of said enantiomer $E_2$. The invention also relates to a composition comprising said enantiomer $E_1$ in which the amount of said enantiomer $E_1$ in the composition is different from the amount of said enantiomer $E_2$ in the composition.

The invention thus relates to a composition comprising a configurational stereoisomer, named enantiomer $E_1$, of bromadiolone, with the exclusion of a racemic mixture of said enantiomer $E_1$ and of another configurational stereoisomer, named enantiomer $E_2$, of bromadiolone different from said enantiomer $E_1$;

said enantiomer $E_1$ having, by chromatographic analysis of a bromadiolone composition comprising four configurational stereoisomers of bromadiolone performed under the conditions described below, a retention time $t_1$;

said enantiomer $E_2$ having, by chromatographic analysis of a bromadiolone composition comprising four configurational stereoisomers of bromadiolone performed under these same conditions, a retention time $t_2$; $t_1$ and $t_2$ being values such that $t_1 < t_2 < t_3 < t_4$; $t_3$ and $t_4$ representing the retention times of configurational stereoisomers of bromadiolone different from said enantiomer $E_1$ and from said enantiomer $E_2$, said analysis being performed at a temperature of 27.3° C.:

on a high-pressure liquid chromatography column of dimensions 150×2 mm, and containing a chiral stationary phase constituted of particles of cellulose tris(3,5-dimethylphenyl carbamate), said particles having a mean size of 3 m and having a mean pore size of 1000 Å;

using, as liquid mobile phase, a mixture formed from acetonitrile (A) and water comprising 0.1% by volume of formic acid (B), with an A/B volume ratio of 80/20 and with a flow rate of the liquid mobile phase in the chromatography column of 0.25 mL/minute;

by injection into the chromatography column of a volume of 1 µL of bromadiolone composition at a concentration of 1 µg of bromadiolone per millilitre of acetonitrile.

The invention thus relates to such a composition comprising said enantiomer $E_1$, with the exclusion of a racemic mixture of said enantiomer $E_1$ and of said enantiomer $E_2$, i.e. with the exclusion of a composition in which said enantiomer $E_1$ and said enantiomer $E_2$ are in equimolar mixture and not optically active. In a composition according to the invention, said enantiomer $E_1$ and said enantiomer $E_2$ are thus not in equimolar and racemic mixture. Said enantiomer $E_1$ and said enantiomer $E_2$ are quantified by chromatographic analysis under the abovementioned conditions and by performing detection of the configurational stereoisomers by absorption photometry or by absorption spectrometry, by adjusting the concentration of bromadiolone in the bromadiolone solution and the volume injected according to the sensitivity of the detector and measuring the value of the area under the peak corresponding to each enantiomer $E_1$ and $E_2$. It is also possible to assay said enantiomer $E_1$ and said enantiomer $E_2$ of any composition comprising bromadiolone by performing detection by mass spectrometry at the outlet of the separating column.

Advantageously and according to the invention, the amount of said enantiomer $E_1$ is greater than the amount of said enantiomer $E_2$ in the composition. Advantageously, said diastereoisomer $D_{1,2}$ of bromadiolone is predominantly in the form of said enantiomer $E_1$ in the composition. Advantageously, a composition according to the invention comprises the diastereoisomer $D_{1,2}$ of bromadiolone predominantly in the form of said enantiomer $E_1$.

Throughout the text, the term "said diastereoisomer $D_{1,2}$ is predominantly in the form of said enantiomer $E_1$" means that the ratio of the amount (on a mass, molar or volume basis) of said enantiomer $E_1$ to the amount (on a corresponding mass, molar or volume basis) of said diastereoisomer $D_{1,2}$ (in all its enantiomeric forms) is greater than 50%.

Thus, in particular, in a composition according to the invention:

the ratio of the amount of said enantiomer $E_1$ to the sum of the amounts of each enantiomer ($E_1$ and $E_2$) of said diastereoisomer $D_{1,2}$ is greater than 0.5 (greater than 50%);

the ratio of the concentration of said enantiomer $E_1$ to the sum of the concentrations of each enantiomer ($E_1$ and $E_2$) of said diastereoisomer $D_{1,2}$ is greater than 0.5 (greater than 50%); and the proportion of said enantiomer $E_1$ in the composition is greater than the proportion of said enantiomer $E_2$ in the composition.

Advantageously and according to the invention, the composition comprises an amount of said enantiomer $E_1$ such that the ratio of this amount to the sum of the amount of said enantiomer $E_1$ and of the amount of said enantiomer $E_2$ in the composition is greater than 50%, especially greater than 60%, in particular greater than 70%, more particularly greater than 80%, preferably greater than 90%, more preferentially greater than 95%, particularly preferentially greater than 98%, even more preferentially greater than 99% or about 100%.

In a particular embodiment, advantageously and according to the invention, the composition comprises an amount of said enantiomer $E_1$ such that the ratio of this amount to the sum of the amount of said enantiomer $E_1$ and of the amount of said enantiomer $E_2$ in the composition is greater than 75%, preferably between 85% and 100% and more preferentially between 90% and 98%.

In another embodiment, advantageously and according to the invention, the composition comprises an amount of said enantiomer $E_1$ such that the ratio of this amount to the sum of the amount of said enantiomer $E_1$ and of the amount of said enantiomer $E_2$ in the composition is between 98% and 100%.

The composition may also comprise an amount of said enantiomer $E_2$ such that the ratio of this amount to the sum of the amount of said enantiomer $E_1$ and of the amount of said enantiomer $E_2$ is less than 50%, especially less than 25%, preferentially between 0% and 25%, in particular less than 10%.

Advantageously and according to the invention, bromadiolone is predominantly in the form of said enantiomer $E_1$ in the composition. The composition thus comprises an amount of said enantiomer $E_1$ such that the ratio of this amount to the amount of bromadiolone in the composition is greater than the ratio of the amount of said enantiomer $E_2$ to the amount of bromadiolone in the composition and greater than the ratio of the amount of each enantiomer (enantiomer $E_3$ and enantiomer $E_4$) of said diastereoisomer $D_{3,4}$ to the amount of bromadiolone in the composition.

Thus, in particular, in a composition according to the invention:

the ratio of the amount of said enantiomer $E_1$ to the amount of bromadiolone is greater than 0.25 (greater than 25%);

the ratio of the amount of said enantiomer $E_1$ to the sum of the amounts of the enantiomers $E_3$ and $E_4$ of said diastereoisomer $D_{3,4}$ and of the enantiomers $E_1$ and $E_2$ of said diastereoisomer $D_{1,2}$ is greater than 0.25 (greater than 25%);

the ratio of the concentration of said enantiomer $E_1$ in the composition to the concentration of bromadiolone in the composition is greater than 0.25 (greater than 25%);

the proportion of said enantiomer $E_1$ in the composition is greater than the proportion of each of the enantiomers $E_3$ and $E_4$ of said diastereoisomer $D_{3,4}$ in the composition and greater than the proportion of said enantiomer $E_2$ in the composition.

Advantageously and according to the invention, the composition comprises an amount of said enantiomer $E_1$ such that the ratio of this amount to the amount of bromadiolone in the composition is greater than 25%, especially greater than 50%, in particular greater than 70%, more particularly greater than 80%, preferably greater than 90%, particularly preferentially greater than 95%, more preferentially greater than 98%, even more preferentially greater than 99% or about 100%.

In a particular embodiment, advantageously and according to the invention, the composition comprises an amount of said enantiomer $E_1$ such that the ratio of this amount to the amount of bromadiolone in the composition is greater than 70%, preferably between 80% and 100% and more preferentially between 90% and 100%.

In another embodiment, advantageously and according to the invention, the composition comprises an amount of said enantiomer $E_1$ such that the ratio of this amount to the amount of bromadiolone in the composition is between 95% and 99%.

In another particular embodiment, advantageously and according to the invention, the composition comprises an amount of said enantiomer $E_1$ such that the ratio of this amount to the amount of bromadiolone in the composition is greater than 95%.

In another embodiment, advantageously and according to the invention, the composition comprises an amount of said enantiomer $E_1$ such that the ratio of this amount to the amount of bromadiolone in the composition is between 98% and 100%, limits inclusive.

In another particularly advantageous embodiment according to the invention, the composition comprises an amount of said enantiomer $E_1$ such that the ratio of this amount to the amount of bromadiolone in the composition is substantially about 100%.

A composition according to the invention may be substantially free of said enantiomer $E_2$, i.e. said enantiomer $E_2$ of said diastereoisomer $D_{1,2}$ may be present in the composition but only in trace amount. A composition according to the invention may also be substantially free of said diastereoisomer $D_{3,4}$, i.e. said diastereoisomer $D_{3,4}$ may be present in the composition but only in trace amount.

Advantageously and according to the invention, the composition is in liquid form and comprises a liquid solvent for bromadiolone. It may be a solution of bromadiolone in a solvent for bromadiolone, with the exclusion of a racemic mixture of said enantiomer $E_1$ and of said enantiomer $E_2$. It may also be a solution of bromadiolone in a solvent for bromadiolone and in which said diastereoisomer $D_{1,2}$ is predominantly in the form of said enantiomer $E_1$.

It may also be a solid comprising bromadiolone, with the exclusion of a racemic mixture of said enantiomer $E_1$ and of said enantiomer $E_2$. It may also be a solid comprising bromadiolone and in which said diastereoisomer $D_{1,2}$ is predominantly in the form of said enantiomer $E_1$. It may also be a solid comprising bromadiolone and in which the bromadiolone is predominantly in the form of said enantiomer $E_1$.

The invention thus also relates to a composition comprising said enantiomer $E_1$ according to the invention, with the exclusion of a racemic mixture of said enantiomer $E_1$ and of said enantiomer $E_2$, said composition being optically active. However, it is not excluded for the composition according to the invention comprising said enantiomer $E_1$, with the exclusion of a racemic mixture of said enantiomer $E_1$ and of said enantiomer $E_2$, to itself be optically inactive.

The invention also relates to the use of a composition according to the invention for the preparation of a rodenticidal bait for target rodent pests.

The invention also relates to a rodenticidal bait comprising a composition according to the invention, and at least one excipient that is edible for target rodent pests.

A rodenticidal bait according to the invention comprises:

at least one excipient that is edible for target rodent pests; and a configurational stereoisomer, named enantiomer $E_1$, of bromadiolone, with the exclusion of a racemic mixture of said enantiomer $E_1$ and of another configurational stereoisomer, named enantiomer $E_2$, of bromadiolone different from said enantiomer $E_1$;

said enantiomer $E_1$ having, by chromatographic analysis of a bromadiolone composition comprising four configurational stereoisomers of bromadiolone performed under the conditions described below, a retention time $t_1$;

said enantiomer $E_2$ having, by chromatographic analysis of a bromadiolone composition comprising four configurational stereoisomers of bromadiolone performed under these same conditions, a retention time $t_2$; $t_1$ and $t_2$ being values such that $t_1<t_2<t_3<t_4$; $t_3$ and $t_4$ representing the retention times of configurational stereoisomers of bromadiolone different from said enantiomer $E_1$ and from said enantiomer $E_2$, said analysis being performed at a temperature of 27.3° C. and under the following conditions:

on a high-pressure liquid chromatography column of dimensions 150×2 mm, and containing a chiral stationary phase constituted of cellulose tris(3,5-dimethylphenyl carbamate) particles, said particles having a mean size of 3 μm and having a mean pore size of 1000 Å;

using, as liquid mobile phase, a mixture formed from acetonitrile (A) and water comprising 0.1% by volume of formic acid (B), with an A/B volume ratio of 80/20 and with a flow rate of the liquid mobile phase in the chromatography column of 0.25 mL/minute;

by injection into the chromatography column of a volume of 1 μL of bromadiolone composition at a concentration of 1 μg of bromadiolone per millilitre of acetonitrile.

Advantageously, a rodenticidal bait according to the invention comprises an excipient that is edible for target rodent pests and said enantiomer $E_1$, with the exclusion of a racemic mixture of said enantiomer $E_1$ and of said enantiomer $E_2$.

The inventors observed that the two diastereoisomers (diastereoisomer $D_{1,2}$ and diastereoisomer $D_{3,4}$) of bromadiolone do not have the same hepatic persistence in target rodent pests and that said diastereoisomer $D_{1,2}$ is in fact the bromadiolone diastereoisomer which is the more persistent in the liver of target rodents, especially of target rodent pests. They observed that, when it is ingested by a target rodent pest, said diastereoisomer $D_{1,2}$ of a rodenticidal bait disappears from the liver of the target rodent pest which has consumed such a rodenticidal bait according to the invention less rapidly than said diastereoisomer $D_{3,4}$.

The inventors who succeeded in separating the enantiomers of said diastereoisomer $D_{1,2}$ and in isolating said enantiomer $E_1$ also discovered that said enantiomer $E_1$ has:

higher anticoagulant activity than the anticoagulant activity of said enantiomer $E_2$ and also higher than the anticoagulant activities of said two enantiomers of said diastereoisomer $D_{3,4}$; and persistence in the liver of target rodent pests that is higher than the persistence in the liver of target rodent pests of said enantiomer $E_2$ and higher than the persistence in the liver of target rodent pests of each enantiomer of said diastereoisomer $D_{3,4}$.

Thus, said enantiomer $E_1$ according to the invention allows the preparation of rodenticidal baits with high efficacy for a reduced amount of bromadiolone ingested.

Such rodenticidal baits comprising said enantiomer $E_1$ as novel rodenticidal agent are able to be used for controlling populations of target rodent pests that are resistant to known rodenticidal treatments.

Advantageously, a rodenticidal bait according to the invention comprises a mass amount of bromadiolone such that the ratio (mass proportion) of this mass amount of bromadiolone to the mass amount of rodenticidal bait is less than 50 ppm, i.e. less than 50 mg of bromadiolone per kilogram of rodenticidal bait. Advantageously, the mass proportion of bromadiolone relative to the rodenticidal bait is greater than 1 ppm. Advantageously, the mass proportion of bromadiolone relative to the amount of rodenticidal bait is between 1 ppm and 50 ppm (1 mg to 50 mg of bromadiolone per kilogram of rodenticidal bait), especially between 1 ppm and 30 ppm (1 mg to 30 mg of bromadiolone per kilogram of rodenticidal bait), preferably between 1 ppm and 20 ppm (1 mg to 20 mg of bromadiolone per kilogram of rodenticidal bait) and even more preferentially between 1 ppm and 10 ppm (1 mg to 10 mg of bromadiolone per kilogram of rodenticidal bait).

Advantageously, a rodenticidal bait according to the invention comprises an amount of said enantiomer $E_1$ such that the ratio of this amount to the amount of bromadiolone in the bait is greater than 70%, more particularly greater than 80%, preferably greater than 90%, particularly preferentially greater than 95%, more preferentially greater than 98%, even more preferentially greater than 99% or about 100%, and of bromadiolone in a mass proportion of less than 25 ppm relative to the rodenticidal bait.

Advantageously and according to the invention, the excipient that is edible for target rodent pests is chosen to allow consumption of the bait by target rodent pests. Advantageously and according to the invention, each edible excipient is non-lethal to target rodent pests. The edible excipient is not in itself rodenticidal.

Advantageously and according to the invention, the edible excipient comprises at least one food chosen from the group formed from cereal seeds—especially hulled cereal seeds—cereal seed meals, cereal seed flours, cereal seed flakes, cereal bran and non-cereal seeds, for example alfalfa seeds—especially in hulled form, in the form of meal, in the form of flour, or in the form of flakes or bran. The edible excipient may comprise any support that can be consumed by target rodent pests.

Advantageously, the edible excipient comprises at least one food chosen from the group formed from foods of plant origin and foods of animal origin. Advantageously, the edible excipient comprises at least one food chosen to stimulate the appetite of the target rodent pests. In particular, this food is chosen from the group formed from seeds of one or more cereals, hulled seeds of one or more cereals, meals of seeds of one or more cereals, flakes of seeds of one or more cereals, bran of one or more cereals and flour of seeds of one or more cereals. By way of example, the cereals are chosen from the group formed from oat, wheat, barley, corn, soybean and rice.

Advantageously, the food is chosen from the group formed from sweetened foods. For example, they may be foods comprising at least one sugar chosen from the group formed from sucrose, lactose, fructose and glucose. It may be a sugar syrup—for example a sugar syrup obtained by hydrolysis of starch—or a sugar syrup obtained by hydrolysis of sucrose (invert sugar syrup), or a beet sugar syrup, or a maple syrup or a sugarcane syrup, or a syrup obtained from a plant of the Stevia genus.

Advantageously, the food is chosen from the group formed from coconut albumen (copra) flakes and flour. Advantageously, the food is chosen from the group formed from walnuts, hazelnuts and almonds—in grated and/or powder form.

Advantageously, the food is chosen from the group formed from plant fats, plant oils (for example rapeseed oil, soybean fat, sunflower oil, cocoa butter, groundnut oil, groundnut butter, corn oil, palm oil), animal fats and animal oils (butter, lard, fish oil).

Advantageously, the food is chosen from the group formed from proteins of plant origin and proteins of animal origin. By way of example, examples that may be mentioned include powdered milk—especially powdered skimmed milk—eggs—especially powdered eggs—protein hydrolysates of animal origin and protein hydrolysates of plant origin.

Advantageously and according to the invention, the rodenticidal bait is chosen from the group formed from solid baits comprising bromadiolone and a solid edible excipient. Advantageously, the rodenticidal bait may be a solid in divided form, for example in the form of balls or granules. Advantageously, the rodenticidal bait may also be a solid in block or paste form that may be consumed by the target rodent pests or a solid material that may be nibbled by the target rodent pests. Advantageously, the solid rodenticidal bait according to the invention may be in the form of a rigid block, a semi-rigid block, a foam, a powder or a gel.

Advantageously, the rodenticidal bait which is in the form of a powder, in the form of a foam or in the form of a gel is suitable for soiling the fur of the target rodent pest(s) and for being ingested by said pest(s) during their grooming.

It may be a solid rodenticidal bait comprising bromadiolone, with the exclusion of a racemic mixture of said enantiomer $E_1$ and of said enantiomer $E_2$. It may also be a solid rodenticidal bait comprising bromadiolone and in which the amount of said enantiomer $E_1$ is greater than the amount of said enantiomer $E_2$. It may also be a solid rodenticidal bait comprising bromadiolone and in which the bromadiolone is predominantly in the form of said enantiomer $E_1$.

Advantageously and according to the invention, the rodenticidal bait is chosen from the group formed from liquid baits comprising bromadiolone and a liquid edible excipient. The rodenticidal bait is then a drink for target rodent pests. It may be a solution of bromadiolone in a solvent for bromadiolone, with the exclusion of a racemic mixture of said enantiomer $E_1$ and of said enantiomer $E_2$. It may also be a solution of bromadiolone in a solvent for bromadiolone and in which the amount of said enantiomer $E_1$ is greater than the amount of said enantiomer $E_2$. It may also be a solution of bromadiolone in a solvent for bromadiolone and in which the bromadiolone is predominantly in the form of said enantiomer $E_1$. It may also be a suspension of bromadiolone in solid form in a liquid medium. It may also be an emulsion of bromadiolone in a liquid medium.

The invention thus also relates to a rodenticidal bait in which the bromadiolone is optically active. However, it is not excluded for the bromadiolone of the rodenticidal bait according to the invention to be optically inactive.

Advantageously, the rodenticidal bait comprises at least one dye. Such a dye makes it possible in particular to give said rodenticidal bait a colour that is readily detectable and identifiable by a person handling the rodenticidal bait.

Advantageously, the rodenticidal bait comprises at least one preserving agent capable of ensuring its conservation during its storage. Advantageously, the rodenticidal bait comprises at least one bittering compound such as denatonium benzoate, also known as Bitrex®, which is intended to reduce the risks of accidental consumption by non-target organisms.

Advantageously, in a particular variant, the composition and the rodenticidal bait according to the invention exclusively comprise bromadiolone, with the exclusion of a racemic mixture of said enantiomer $E_1$ and of said enantiomer $E_2$, as rodenticidal substance. In particular, the composition and the rodenticidal bait according to the invention are free of any other anticoagulant substance for rodenticidal use different from bromadiolone. However, in this variant according to the invention, the composition and the rodenticidal bait may comprise any pest-control substance other than a rodenticide, such as an insecticidal and/or acaricidal substance.

Advantageously, in another particular variant, the composition and the rodenticidal bait according to the invention comprise bromadiolone, with the exclusion of a racemic mixture of said enantiomer $E_1$ and of said enantiomer $E_2$, and at least one other substance different from bromadiolone as rodenticidal substance. This other rodenticidal substance different from bromadiolone may be another anticoagulant substance—especially of the anti-vitamin K type or not—or another non-anticoagulant rodenticidal substance.

The invention also relates to a process for controlling target rodent pests, in which there is spread an amount of rodenticidal bait comprising:

at least one excipient that is edible for target rodent pests; and a configurational stereoisomer, named enantiomer $E_1$, of bromadiolone, with the exclusion of a racemic mixture of said enantiomer $E_1$ and of another configurational stereoisomer, named enantiomer $E_2$, of bromadiolone different from said enantiomer $E_1$;

said enantiomer $E_1$ having, by chromatographic analysis of a bromadiolone composition comprising four configurational stereoisomers of bromadiolone performed under the conditions described below, a retention time $t_1$;

said enantiomer $E_2$ having, by chromatographic analysis of a bromadiolone composition comprising four configurational stereoisomers of bromadiolone performed under these same conditions, a retention time $t_2$; $t_1$ and $t_2$ being values such that $t_1 < t_2 < t_3 < t_4$; $t_3$ and $t_4$ representing the retention times of configurational stereoisomers of bromadiolone different from said enantiomer $E_1$ and from said enantiomer $E_2$, said analysis being performed at a temperature of 27.3° C. and under the following conditions:

on a high-pressure liquid chromatography column of dimensions 150×2 mm, and containing a chiral stationary phase constituted of particles of cellulose tris(3,5-dimethylphenyl carbamate), said particles having a mean size of 3 µm and having a mean pore size of 1000 Å;

using, as liquid mobile phase, a mixture formed from acetonitrile (A) and water comprising 0.1% by volume of formic acid (B), with an A/B volume ratio of 80/20 and with a flow rate of the liquid mobile phase in the chromatography column of 0.25 mL/minute;

by injection into the chromatography column of a volume of 1 µL of bromadiolone composition at a concentration of 1 µg of bromadiolone per millilitre of acetonitrile.

The invention also relates to a process for controlling target rodent pests, in which there is spread an amount of rodenticidal bait according to the invention, said amount of bait being sufficient to be rodenticidal.

Advantageously and according to the invention, an amount of rodenticidal bait comprising said enantiomer $E_1$, with the exclusion of a racemic mixture of said enantiomer $E_1$ and of said enantiomer $E_2$, is spread. An amount of rodenticidal bait is spread, said rodenticidal bait comprising a reduced amount of bromadiolone and being chosen to limit secondary intoxication of non-target species which consume poisoned rodents. Advantageously, the amount of said enantiomer $E_1$ in the rodenticidal bait may be greater than the amount of said enantiomer $E_2$ in the rodenticidal bait. In such a process, advantageously and according to the invention, bromadiolone may be predominantly in the form of said enantiomer $E_1$.

Advantageously and as a variant according to the invention, the following are chosen in combination:

the edible excipient;

an amount of said enantiomer $E_1$ different from the amount of said enantiomer $E_2$ in the rodenticidal bait;

a proportion of said enantiomer $E_1$ relative to the bromadiolone; and a mass proportion of bromadiolone in the rodenticidal bait; and an amount of spread rodenticidal bait;

so that target rodent pests consume an amount of bromadiolone that is sufficient to be lethal to said target rodent pests which consume said bait in the course of a single period of 24 consecutive hours.

A rodenticidal bait according to this variant of the invention is a bait that is mortal in a single intake, or a "one-shot" bait. Advantageously and according to this variant of the invention, the mass proportion of bromadiolone in the bait is less than 50 ppm, especially between 5 ppm and 25 ppm.

Advantageously and in another variant according to the invention, the following are chosen in combination:

the edible excipient;

an amount of said enantiomer $E_1$ different from the amount of said enantiomer $E_2$ in the rodenticidal bait;

a proportion of said enantiomer $E_1$ relative to the bromadiolone; and a mass proportion of bromadiolone in the rodenticidal bait; and an amount of spread rodenticidal bait;

so that target rodent pests consume an amount of bromadiolone:

which is non-lethal to target rodent pests, i.e. which is generally non-lethal to target rodent pests which consume said bait over a period of 24 consecutive hours; and which is sufficient to be lethal to target rodent pests which consume said bait over several 24-hour periods.

Advantageously and according to the invention, the 24-hour periods are consecutive.

This other variant of the invention is thus also directed towards a process for controlling target rodent pests, in which there is spread an amount of rodenticidal bait that is lethal for target rodent pests which durably consume this rodenticidal bait and non-lethal for non-target rodents or animals which accidentally consume this rodenticidal bait. This is then referred to as a "multi-dose" or "multi-feeding" control process. In such a process according to the invention, the consumption of rodenticidal bait by a target rodent pest over a period of 24 hours is insufficient to result in the death of said rodent, whereas repeated consumption of rodenticidal bait over at least two consecutive days can result in the death of the target rodent pest.

This other variant of the invention is thus directed towards a process for controlling a population of target rodent pests, in which target rodent pests are provided with an amount of rodenticidal bait that is liable to be ingested by the target rodent pests, said amount of rodenticidal bait being sufficient to kill target rodent pests which consume said rodenticidal bait over several days.

Advantageously, in this other variant of a process according to the invention, the amount of rodenticidal bait spread, the mass proportion of bromadiolone relative to the rodenticidal bait and the proportion of said enantiomer $E_1$ relative to the proportion of said enantiomer $E_2$ are adapted so that the consumption of the rodenticidal bait is lethal to target rodent pests which daily consume bait over at least two 24-hour periods, especially from 3 to 7 periods, said periods being consecutive.

Advantageously, in this other variant of a process according to the invention, since the proportion of said enantiomer $E_1$ is greater than 95%—especially about 100%—relative to the bromadiolone, the mass proportion of bromadiolone relative to the rodenticidal bait may be between 1 ppm and 25 ppm, especially between 1 ppm and 15 ppm and in particular about 10 ppm.

In a process according to the invention, target rodent pests are provided with an amount of rodenticidal bait that is sufficient to satisfy the daily appetite of the target rodent pests, said rodenticidal bait predominantly comprising said enantiomer $E_1$ relative to said diastereoisomer $D_{1,2}$ and relative to the bromadiolone.

In a process according to the invention, the amount of rodenticidal bait spread, the amount of said enantiomer $E_1$ relative to said enantiomer $E_2$ and relative to the bromadiolone and the mass proportion of bromadiolone relative to the rodenticidal bait are adapted so as to allow consumption of rodenticidal bait for several days by target rodent pests, while at the same time limiting:

the risks of primary intoxication of non-target mammals and birds which are liable to consume such a rodenticidal bait only occasionally and accidentally;

the risks of secondary intoxication, for example of predators of target rodents, which are liable to consume target rodents—dead or live—that have ingested an amount of said bait.

The invention also relates to a configurational stereoisomer of bromadiolone, to a process for obtaining this configurational stereoisomer, to a composition comprising this configurational stereoisomer, to a rodenticidal bait and to a process for controlling target rodent pests, characterized in combination by all or some of the characteristics mentioned hereinabove or hereinbelow.

Other aims, characteristics and advantages of the invention will emerge on reading the following description and the examples, which are given for purely non-limiting purposes and which refer to the attached figures, in which.

Separation of the Configurational Stereoisomers of Bromadiolone

Figure 1:
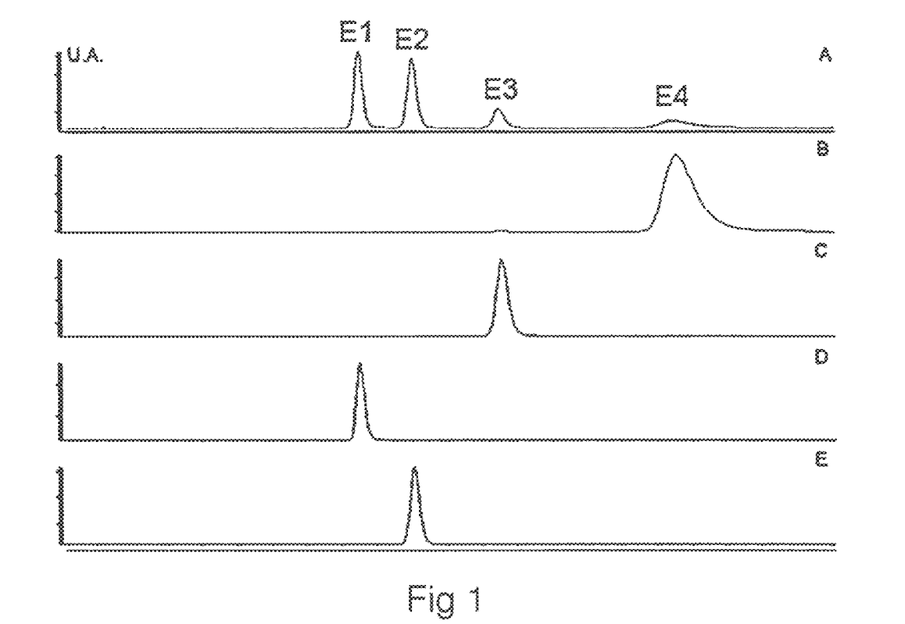
FIG. 1 represents a chromatographic analysis of a mixture of the configurational stereoisomers of bromadiolone on a chiral column and of each configurational stereoisomer of bromadiolone on the same chiral column.

Separation of the configurational stereoisomers of bromadiolone is performed by high-pressure liquid chromatography on a LUX® Cellulose-1 chiral column (Phenomenex, Le Pecq, France) containing a chiral stationary phase constituted of particles of cellulose tris(3,5-dimethylphenyl carbamate), said particles having a mean size of 3 µm and having a mean pore size of 1000 Å. A mixture formed from acetonitrile (A) and water comprising 0.1% by volume of formic acid (B), with an A/B volume ratio of 80/20 and with a flow rate of 0.25 mL/minute in the chromatography column, is used as mobile phase. The concentration of the composition to be analysed is 1 µg of bromadiolone per millilitre of acetonitrile and the volume injected onto the column is 1 µL. Detection is performed by tandem mass spectrometry (MS/MS) in negative electrospray ionization (ESI) mode. The temperature of the nebulizer gas is 350° C.

and its flow rate is 8 L/minute. The pressure of the nebulizer gas is brought to 2700 hPa. In particular, the MRM ("Multiple Reaction Monitoring") transitions m/z 525.1→250.1 and m/z 525.1→181, corresponding to the bromadiolone signal, are detected. An example of a chromatogram is presented in FIG. 1.

The retention time values for each of the configurational stereoisomers of bromadiolone are:

for enantiomer $E_1$ of said diastereoisomer $D_{1,2}$, $t_1$=4.3 min;

for enantiomer $E_2$ of said diastereoisomer $D_{1,2}$, $t_2$=5.0 min;

for enantiomer $E_3$ of said diastereoisomer $D_{3,4}$, $t_3$=6.3 min; and for enantiomer $E_4$ of said diastereoisomer $D_{3,4}$, $t_4$=8.8 min.

The retention time values $t_1$, $t_2$, $t_3$ and $t_4$ are liable to vary, according to the chromatographic conditions. However, in any case, under these conditions (choice of these mobile and stationary phases), the order of elution of the configurational stereoisomers of bromadiolone remains unchanged. As a guide, the retention time values for each of the configurational stereoisomers of bromadiolone may vary with a variation of a few degrees Celsius of the temperature of the chromatography column. For said enantiomer $E_1$, the retention time ($t_1$) may range between 4.1 min and 4.4 min. For said enantiomer $E_2$, the retention time ($t_2$) may range between 4.8 min and 5.2 min. For said enantiomer $E_3$, the retention time ($t_3$) may range between 6.0 min and 6.6 min. For said enantiomer $E_4$, the retention time ($t_4$) may range between 8.3 min and 9.0 min.

Extraction of Bromadiolone from the Liver of Rats Treated with Bromadiolone

Homogenization of the Liver Sample

About 0.525 g (+0.025 g) of rat liver is weighed out accurately and placed in a 50 mL polypropylene tube. 10 mL of acetone are added and the suspension is homogenized using an Ultra-Turrax® homogenizer/disperser for a time of about 30 seconds. The homogenizer/disperser shaft is rinsed with hot water and then twice with 20 mL of acetone in a polypropylene tube. The homogenate is centrifuged for 5 minutes at a centrifugation speed of 3000 rpm (revolutions per minute). The supernatant is collected and transferred into a test tube. The sample is subjected to evaporation under a stream of nitrogen ($N_2$) at a temperature of 40° C. so as to form a dry extract.

Lipid Removal 1 mL of acetonitrile is added to the tube containing the dry extract so as to dissolve it. The acetonitrile solution is washed twice successively with 1 mL of hexane. The lipid-free extract is dried under a stream of nitrogen ($N_2$) at a temperature of 40° C. and is then taken up in 0.5 mL of methanol and dissolved by vortex stirring. 0.5 mL of ultrapure (Milli-Q) water is then added. The sample is vortex-homogenized.

Solid-Phase Extraction (SPE) of Bromadiolone 1 mL of dichloromethane ($CH_2Ce_2$), then 1 mL of methanol ($CH_3OH$), then 1 mL of ultra-pure (Milli-Q) water are passed through an Oasis HLB 1 cc cartridge (WAT094225, Waters). The lipid-free liver extract (1 mL MeOH/Milli-Q $H_2O$) containing bromadiolone is then loaded onto the top of the preconditioned cartridge. The liver extract penetrates through the cartridge by gravity on contact with the solid phase of the cartridge. 1 mL of washing solution formed from methanol ($CH_3OH$) and ultra-pure water ($H_2O$) in a 90/10 volume proportion is loaded onto the top of the cartridge. The cartridge is dried by suction under vacuum connected to the bottom of the cartridge. 1 mL of eluting solution formed from dichloromethane ($CH_2Ce_2$) and methanol ($CH_3OH$) in a 90/10 volume proportion is then loaded onto the top of the cartridge and an eluate comprising bromadiolone is collected at the bottom of the cartridge. The solvent of the eluate is evaporated off under a stream of nitrogen ($N_2$) at a temperature of 40° C. The sample is taken up in 0.5 mL of acetonitrile (NC—$CH_3$) and the acetonitrile solution containing bromadiolone is filtered through a 0.2 μm filter.

Hepatic Persistence of the Configurational Stereoisomers of Bromadiolone in Rats A mixture of diastereoisomers (diastereoisomer $D_{1,2}$ and diastereoisomer $D_{3,4}$) of bromadiolone dissolved in a mixture of vegetable oil and 5% of DMSO is administered by tube feeding ("per os") to 8-week-old male and female "Sprague-Dawley" SD rats weighing about 200 g. The molar proportion of said diastereoisomer $D_{1,2}$ is 56% and the molar proportion of said diastereoisomer $D_{3,4}$ is 44%.

Tube-feeding solution is administered (on D0) so that the amount of bromadiolone ingested by each rat is about 13 mg per kilogram of rat. To avoid haemorrhage, the tube-fed rats are treated daily by subcutaneous administration of a dose of vitamin K1 (as haemorrhage antidote) at a rate of 0.1 U per 200 g of live rat weight.

On D1 (D+1), D3 (D+3) and D7 (D+7) after tube feeding, four rats anaesthetized beforehand with isoflurane are euthanized, the liver of the euthanized rats is removed, the bromadiolone is then extracted from the liver and the amount of each of the configurational stereoisomers of bromadiolone is assayed by high-pressure liquid chromatography analysis on a chiral column as described above. The area under the peaks of the chromatogram obtained is measured and each configurational stereoisomer of bromadiolone is quantified by comparison with a calibration curve.

Figure 2:
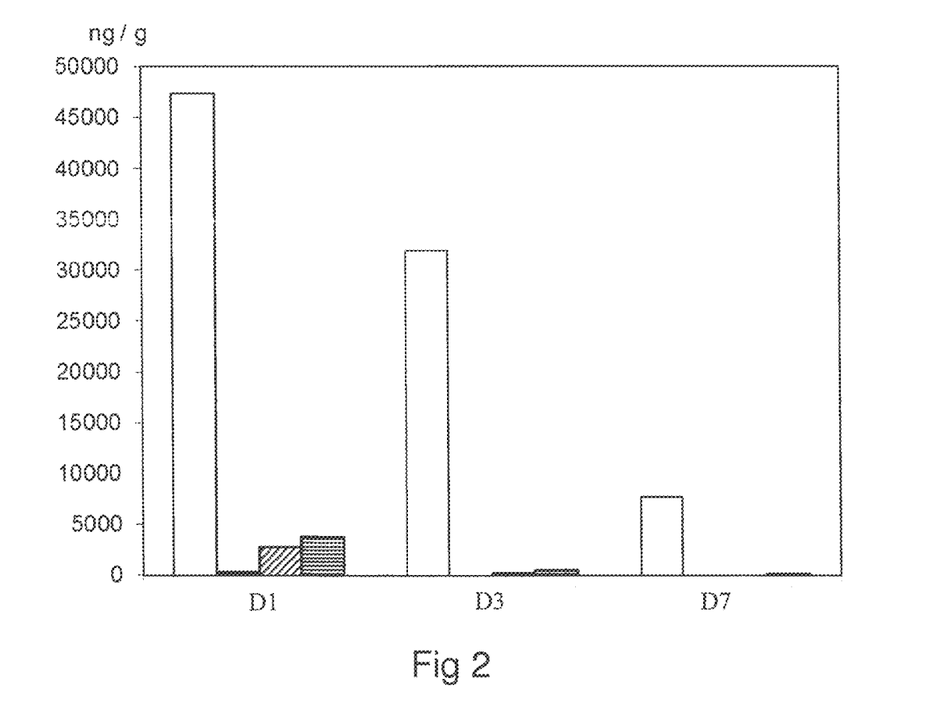
FIG. 2 is a histogram graph representation of the change in the hepatic concentration of each of the configurational stereoisomers of bromadiolone in rats tube-fed with bromadiolone.

The results are shown in FIG. 2. Enantiomer $E_1$ is represented by white columns, enantiomer $E_2$ is represented by black columns, enantiomer $E_3$ is represented by oblique-hatched columns and enantiomer $E_4$ is represented by horizontally-hatched columns. Enantiomer $E_1$ has the longest persistence in rat liver of the four enantiomers $E_1$, $E_2$, $E_3$ and $E_4$. This property makes enantiomer $E_1$ the preferential candidate for preparing a rodenticidal bait with a low dose of rodenticidal agent, in particular for its use in a "multi-feeding" process.

Anticoagulant Power of Each Configurational Stereoisomer of Bromadiolone

The following are administered to male laboratory rats (OFA, Sprague-Dawley 200 g) by tube feeding on D0:

a composition comprising enantiomer $E_1$ in a proportion of 1.5 mg of said enantiomer $E_1$ per kilogram of rat; or a composition comprising enantiomer $E_2$ in a proportion of 1.5 mg of said enantiomer $E_2$ per kilogram of rat; or a composition comprising enantiomer $E_3$ in a proportion of 1.5 mg of said enantiomer $E_3$ per kilogram of rat; or a composition comprising enantiomer $E_4$ in a proportion of 1.5 mg of said enantiomer $E_4$ per kilogram of rat.

On these rats, blood is collected on D1, D3, D7 and D14 and measurement of the coagulation time (Quick time, expressed in seconds) of the plasma is performed using the "Neoplastine CI Determination of Prothrombin Time" kit (Diagnostica Stago, Asnibre, France) by measurement on a Thrombotimer Option 2 Plus machine (Behnk Electronik, Norderstedt, Germany).

Figure 3:
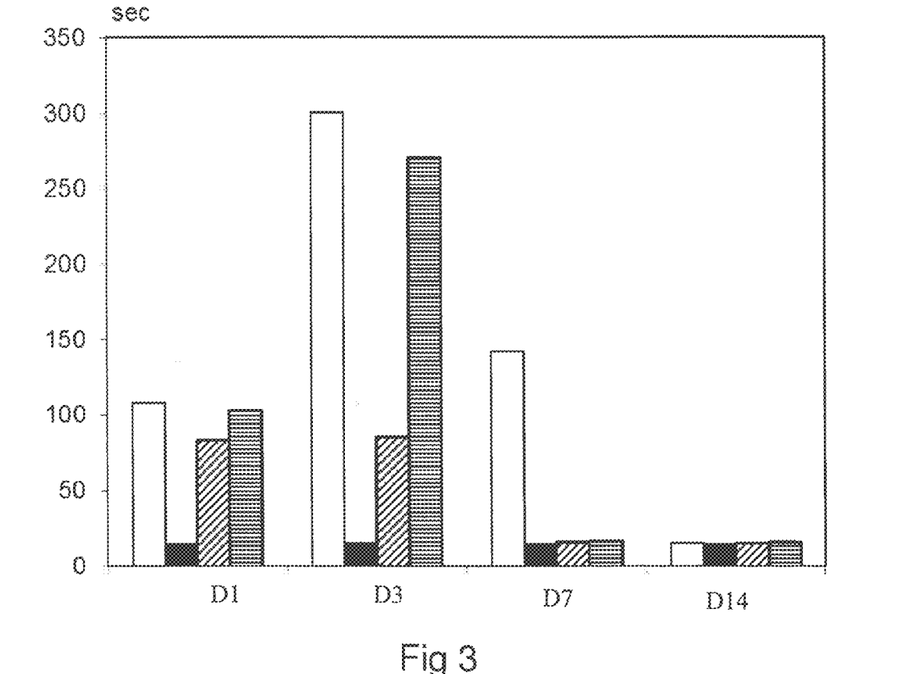
FIG. 3 is a histogram representation of the coagulation time (Quick time) of rats tube-fed with each of the configurational stereoisomers of bromadiolone.

The results obtained are given in FIG. 3, in which:

the white histogram bars correspond to the coagulation time of the rats treated with said enantiomer $E_1$ according to the invention;

the black histogram bars correspond to the coagulation time of the rats treated with said enantiomer $E_2$;

the oblique-hatched histogram bars correspond to the coagulation time of the rats treated with said enantiomer $E_3$; and the horizontally-hatched histogram bars correspond to the coagulation time of the rats treated with said enantiomer $E_4$.

As a guide, the normal value of the coagulation time for untreated rats is about 10 to 20 seconds.

Ingestion of a dose of 1.5 mg per kilogram of rat of said enantiomer $E_1$ according to the invention is sufficient to maintain an anticoagulant effect up to D7.

Hepatic Persistence of Each Configurational Stereoisomer of Bromadiolone

The liver of the rats treated above is removed for the purposes of comparative analysis of the anticoagulant power of the configurational stereoisomers of bromadiolone, the bromadiolone is then extracted from the liver and the amount of each of the configurational stereoisomers of bromadiolone is assayed by high-pressure liquid chromatography analysis on a chiral column as described above. The area under the peaks of the chromatogram obtained is measured and each configurational stereoisomer of bromadiolone is quantified by comparison with a calibration curve. Enantiomers $E_1$, $E_2$, $E_3$ and $E_4$ of bromadiolone present in the rat liver are assayed. The hepatic persistence of each enantiomer is expressed in micrograms (μg) of enantiomer per gram (g) of rat liver.

Figure 4:
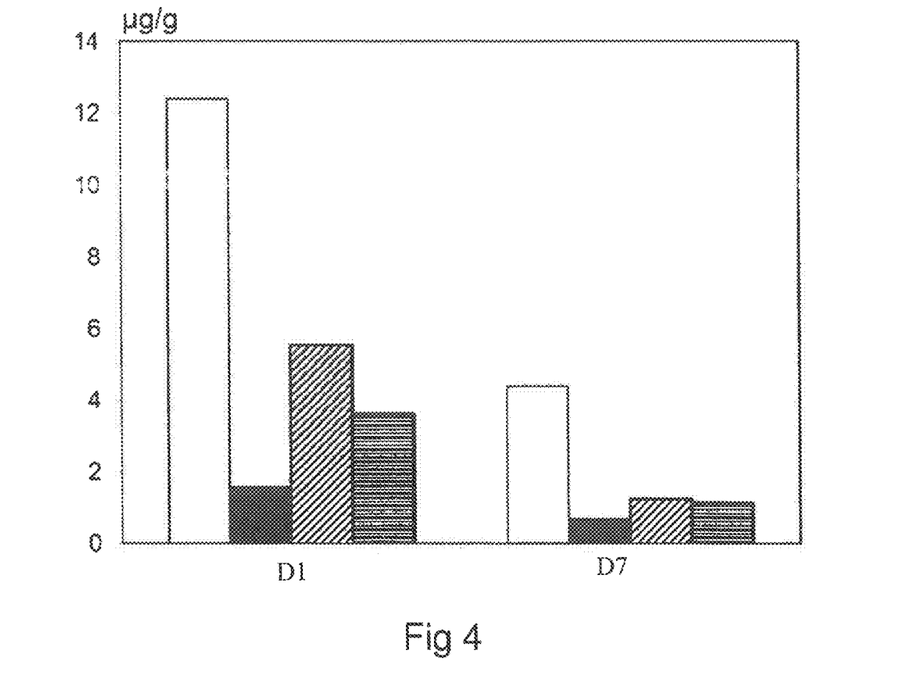
FIG. 4 is a histogram graph representation of the hepatic concentration of each configurational stereoisomer of bromadiolone in rats tube-fed with a single configurational stereoisomer of bromadiolone.

The results are shown in FIG. 4, in which:

the white histogram bar corresponds to the persistence of said enantiomer $E_1$ according to the invention in the liver of rats treated with said enantiomer $E_1$;

the black histogram bar corresponds to the persistence of said enantiomer $E_2$ in the liver of rats treated with said enantiomer $E_2$;

the oblique-hatched histogram bar corresponds to the persistence of enantiomer $E_3$ of said diastereoisomer $D_{3,4}$ of bromadiolone in the liver of rats treated with said enantiomer $E_3$; and the horizontally-hatched histogram bar corresponds to the persistence of enantiomer $E_4$ of said diastereoisomer $D_{3,4}$ of bromadiolone in the liver of rats treated with said enantiomer $E_4$.

Said enantiomer $E_1$ according to the invention has the highest hepatic persistence among the bromadiolone enantiomers. This property makes enantiomer $E_1$ the preferential candidate for preparing a rodenticidal bait comprising a low proportion of rodenticidal substance, in particular for its use in a "multi-feeding" process.

It goes without saying that the invention may be the subject of numerous implementation variants and applications. In particular, a composition, a rodenticidal bait and a process for controlling target rodent pests are subject to an infinite number of variants both in the formulation of the bait and in the embodiments of the process.

The invention claimed is:

1. Configurational stereoisomer, named enantiomer $E_1$, of bromadiolone, said enantiomer $E_1$ being in an isolated state and presenting, under chromatographic analysis of a composition comprising four configurational stereoisomers of bromadiolone performed under the conditions described below, a retention time $t_1$ having a value such that $t_1<t_2<t_3<t_4$;

$t_2$, $t_3$ and $t_4$ being the retention times of the configurational stereoisomers of bromadiolone different from said enantiomer $E_1$, said analysis being performed at a temperature of 27.3° C. and under the following conditions:

using a high-pressure liquid chromatography column of dimensions 150×2 mm, and containing a chiral stationary phase constituted of particles of cellulose tris(3,5-dimethylphenyl carbamate), said particles having a mean size of 3 μm and having a mean pore size of 1000 Å, and;

using, as liquid mobile phase, a mixture formed from acetonitrile (A) and water comprising 0.1% by volume of formic acid (B), with an AB volume ratio of 80/20 and with a flow rate of the liquid mobile phase in the chromatography column of 0.25 mL/minute, and;

by injection into the chromatography column of a volume of 1 μL of bromadiolone composition at a concentration of 1 μg of bromadiolone per millilitre of acetonitrile.

2. Composition comprising a configurational stereoisomer, named enantiomer $E_1$, of bromadiolone, with the exclusion of a racemic mixture of said enantiomer $E_1$ and of another configurational stereoisomer, named enantiomer $E_2$, of bromadiolone different from said enantiomer $E_1$, said enantiomer $E_1$ and said enantiomer $E_2$ being enantiomers of one diastereoisomer of the two diastereoisomers of bromadiolone;

said enantiomer $E_1$ having, by chromatographic analysis of a bromadiolone composition comprising four configurational stereoisomers of bromadiolone performed under the conditions described below, a retention time $t_1$;

said enantiomer $E_2$ having, by chromatographic analysis of a bromadiolone composition comprising four configurational stereoisomers of bromadiolone performed under these same conditions, a retention time $t_2$;

$t_1$ and $t_2$ being values such that $t_1<t_2<t_3<t_4$;

$t_3$ and $t_4$ representing the retention times of configurational stereoisomers of bromadiolone different from said enantiomer $E_1$ and from said enantiomer $E_2$, said analysis being performed at a temperature of 27.3° C. and under the following conditions:

using a high-pressure liquid chromatography column of dimensions 150×2 mm, and containing a chiral stationary phase constituted of particles of cellulose tris(3,5-dimethylphenyl carbamate) particles, said particles having a mean size of 3 μm and having a mean pore size of 1000 Å, and;

using, as liquid mobile phase, a mixture formed from acetonitrile (A) and water comprising 0.1% by volume of formic acid (B), with an AB volume ratio of 80/20 and with a flow rate of the liquid mobile phase in the chromatography column of 0.25 mL/minute;

by injection into the chromatography column of a volume of 1 μL of bromadiolone composition at a concentration of 1 μg of bromadiolone per millilitre of acetonitrile.

3. Composition according to claim 2, wherein the amount of said enantiomer $E_1$ is greater than the amount of said enantiomer $E_2$ in the composition.

4. Composition according to claim 2, wherein the bromadiolone is predominantly in the form of said enantiomer $E_1$ in the composition.

5. Composition according to claim 2, comprising an amount of said enantiomer $E_1$ such that the ratio of this amount to the amount of bromadiolone in the composition is greater than 25%.

6. Composition according to claim 2, comprising an amount of said enantiomer $E_1$ such that the ratio of this amount to the amount of bromadiolone in the composition is greater than 95%.

7. Rodenticidal bait comprising a composition according to claim 2 and at least one excipient that is edible for target rodent pests.

8. Bait according to claim 7, wherein the edible excipient comprises at least one food selected from the group consisting of cereal seeds, cereal seed meals, cereal seed flours, cereal seed flakes, cereal bran and non-cereal seeds.

9. Bait according to claim 7, comprising a mass amount of bromadiolone such that the ratio of this mass amount of bromadiolone to the mass amount of rodenticidal bait is less than 50 ppm.

10. Process for controlling target rodent pests, in which there is spread an amount of rodenticidal bait comprising:
at least one excipient that is edible for target rodent pests; and
a configurational stereoisomer, named enantiomer $E_1$, of bromadiolone, with the exclusion of a racemic mixture of said enantiomer $E_1$ and of another configurational stereoisomer, named enantiomer $E_2$, of bromadiolone different from said enantiomer $E_1$ said enantiomer $E_1$ and said enantiomer $E_2$ being enantiomers of one diastereoisomer of the two diastereoisomers of bromadiolone;
said enantiomer $E_1$ presenting, under chromatographic analysis of a bromadiolone composition comprising four configurational stereoisomers of bromadiolone performed under the conditions described below, a retention time $t_1$;
said enantiomer $E_2$ having, by chromatographic analysis of a bromadiolone composition comprising four configurational stereoisomers of bromadiolone performed under these same conditions, a retention time $t_2$;
$t_1$ and $t_2$ being values such that $t_1 < t_2 < t_3 < t_4$;
$t_3$ and $t_4$ representing the retention times of configurational stereoisomers of bromadiolone different from said enantiomer $E_1$ and from said enantiomer $E_2$, said analysis being performed at a temperature of 27.3° C. and under the following conditions:
using a high-pressure liquid chromatography column of dimensions 150×2 mm, and containing a chiral stationary phase constituted of particles of cellulose tris(3,5-dimethylphenyl carbamate), said particles having a mean size of 3 μm and having a mean pore size of 1000 Å, and;
using, as liquid mobile phase, a mixture formed from acetonitrile (A) and water comprising 0.1% by volume of formic acid (B), with an A/B volume ratio of 80/20 and with a flow rate of the liquid mobile phase in the chromatography column of 0.25 mL/minute, and;
by injection into the chromatography column of a volume of 1 μL of bromadiolone composition at a concentration of 1 μg of bromadiolone per millilitre of acetonitrile.

11. Chromatographic process for obtaining said enantiomer $E_1$ according to claim 1, in which:
a high-pressure liquid chromatography column of dimensions 150×2 mm, and containing a chiral stationary phase constituted of cellulose tris(3,5-dimethylphenyl carbamate) particles, is chosen, said particles having a mean size of 3 μm and having a mean pore size of 1000 Å, and;
a mixture formed from acetonitrile (A) and water comprising 0.1% by volume of formic acid (B), with an A/B volume ratio of 80/20, is chosen as liquid mobile phase;
the separation is performed at room temperature;
a liquid composition containing said enantiomer $E_1$ dissolved in acetonitrile is introduced into the top of the chromatography column; and then
the liquid mobile phase is passed at a flow rate of 0.25 mL/min through the chromatography column after the liquid composition, and a fraction of the mobile phase comprising said enantiomer $E_1$ is collected at the column outlet, separately from the configurational stereoisomers of bromadiolone different from said enantiomer $E_1$, and with a retention time $t_1$ having a value such that $t_1 < t_2 < t_3 < t_4$;
$t_2$, $t_3$ and $t_4$ being the retention times of each of the configurational stereoisomers of bromadiolone different from said enantiomer $E_1$; and
the liquid mobile phase of said fraction is removed so as to obtain said enantiomer $E_1$.

12. Composition according to claim 3, wherein the bromadiolone is predominantly in the form of said enantiomer $E_1$ in the composition.

13. Composition according to claim 3, comprising an amount of said enantiomer $E_1$ such that the ratio of this amount to the amount of bromadiolone in the composition is greater than 25%.

14. Composition according to claim 4, comprising an amount of said enantiomer $E_1$ such that the ratio of this amount to the amount of bromadiolone in the composition is greater than 25%.

15. Composition according to claim 3, comprising an amount of said enantiomer $E_1$ such that the ratio of this amount to the amount of bromadiolone in the composition is greater than 95%.

16. Composition according to claim 4, comprising an amount of said enantiomer $E_1$ such that the ratio of this amount to the amount of bromadiolone in the composition is greater than 95%.

17. Composition according to claim 5, comprising an amount of said enantiomer $E_1$ such that the ratio of this amount to the amount of bromadiolone in the composition is greater than 95%.

18. Rodenticidal bait comprising a composition according to claim 3 and at least one excipient that is edible for target rodent pests.

19. Rodenticidal bait comprising a composition according to claim 4 and at least one excipient that is edible for target rodent pests.

20. Rodenticidal bait comprising a composition according to claim 5 and at least one excipient that is edible for target rodent pests.

* * * * *